US012741931B2

(12) United States Patent
Hennum et al.

(10) Patent No.: US 12,741,931 B2
(45) Date of Patent: Sep. 22, 2026

(54) PROCESS FOR THE PREPARATION OF IOPAMIDOL

(71) Applicant: GE HEALTHCARE AS, Oslo (NO)

(72) Inventors: Martin Hennum, Oslo (NO); Lone Aanerud Omtvedt, Oslo (NO); Ole Magne Homestad, Lindesnes (NO); Sumihar H.D. Silalahi, Lindesnes (NO); Siw Anette Helle, Lindesnes (NO); Mari Brusletten, Lindesnes (NO); Lars Terje Holmaas, Lindesnes (NO)

(73) Assignee: GE HEALTHCARE AS, Oslo (NO)

( * ) Notice: Subject to any disclaimer, the term of this patent is extended or adjusted under 35 U.S.C. 154(b) by 518 days.

(21) Appl. No.: 18/013,440

(22) PCT Filed: Jun. 29, 2021

(86) PCT No.: PCT/EP2021/067871
§ 371 (c)(1),
(2) Date: Dec. 28, 2022

(87) PCT Pub. No.: WO2022/002953
PCT Pub. Date: Jan. 6, 2022

(65) Prior Publication Data

US 2023/0250050 A1 Aug. 10, 2023

(30) Foreign Application Priority Data

Jun. 29, 2020 (GB) .................................... 2009917

(51) Int. Cl.
*C07C 231/02* (2006.01)
*C07C 237/46* (2006.01)

(52) U.S. Cl.
CPC .......... *C07C 231/02* (2013.01); *C07C 237/46* (2013.01)

(58) Field of Classification Search
None
See application file for complete search history.

(56) References Cited

U.S. PATENT DOCUMENTS 4,364,921 A * 12/1982 Speck .................. A61K 31/165 424/9.454
5,698,739 A * 12/1997 Sovak ................ A61K 49/0452 564/153

(Continued)

FOREIGN PATENT DOCUMENTS

CN 103382160 A 11/2013
CN 110023279 A 7/2019

(Continued)

OTHER PUBLICATIONS

Search Report received in German Application No. 2009917.2 dated Dec. 1, 2020, 1 page.

(Continued)

*Primary Examiner* — Amy C Bonaparte
(74) *Attorney, Agent, or Firm* — Lathrop GPM LLP; Malaika O.D. Tyson

(57) ABSTRACT

The present invention provides a process for the preparation of a compound of Formula (II):

(Continued)

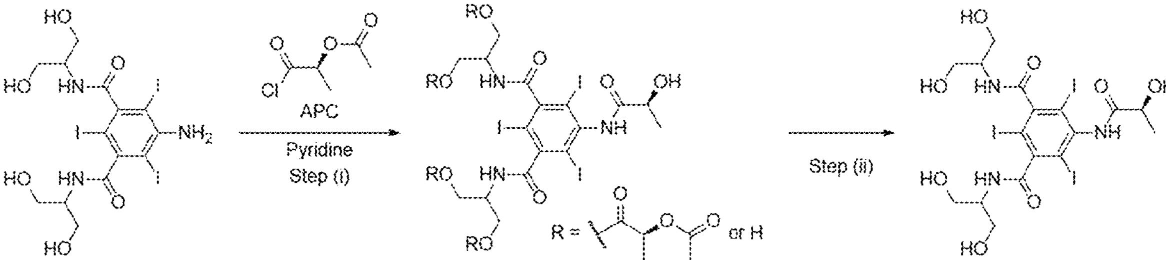

Compound of Formula (I)

Compound of Formula (II)

Compound of Formula (III)
Iopamidol

Formula (II)

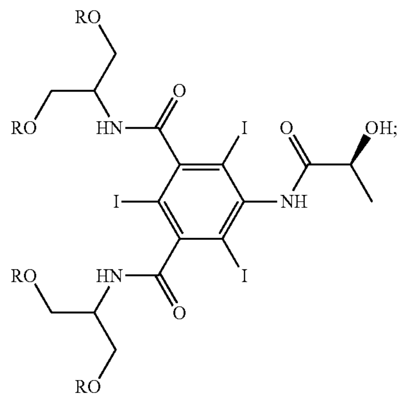

Formula (I)

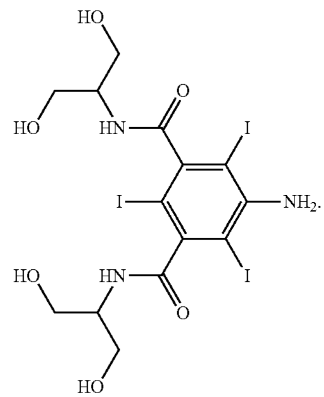

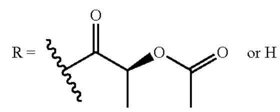

wherein the process comprises:

(i) reacting a compound of Formula (I) with pyridine and 2-acetyloxypropanoyl chloride (APC) to give a compound of Formula (II), wherein the compound of Formula (I) has the following structure:

9 Claims, 3 Drawing Sheets

(56) References Cited

U.S. PATENT DOCUMENTS

| | | | |
|---|---|---|---|
| 5,817,861 | A | 10/1998 | Villa et al. |
| 6,262,303 | B1 | 7/2001 | De Santis et al. |
| 2002/0170860 | A1 | 11/2002 | Wang et al. |

FOREIGN PATENT DOCUMENTS

| | | | | |
|---|---|---|---|---|
| GB | 1472050 | A | | 4/1977 |
| IN | 186589 | B | * | 10/2001 |
| JP | H10-7636 | A | | 1/1998 |
| JP | 2002-524549 | A | | 8/2002 |
| JP | 2005-281207 | A | | 10/2005 |
| JP | 2018-517705 | A | | 7/2018 |
| JP | 2019-535802 | A | | 12/2019 |
| WO | WO 2000/015602 | A1 | | 3/2000 |
| WO | 0029372 | A1 | | 5/2000 |
| WO | 0244125 | A1 | | 6/2002 |
| WO | 0244132 | A1 | | 6/2002 |
| WO | WO 2016/193740 | A1 | | 12/2016 |
| WO | WO 2018/104228 | A1 | | 6/2018 |

OTHER PUBLICATIONS

China Intellectual Property Office, "1st Office Action," regarding Application No. 202180046412.7, 15 pages with translation, dated Feb. 24, 2025.

Japanese Office Action for Japanese Application No. 2022-580886, mailed Mar. 11, 2025.

* cited by examiner iopamidol 1,3-ABA iopamidol

Compound of Formula (I)

Compound of Formula (II)

Compound of Formula (III)
Iopamidol

PROCESS FOR THE PREPARATION OF IOPAMIDOL

TECHNICAL FIELD OF THE INVENTION

The present invention concerns X-ray contrast agents and in particular methods to manufacture iodinated X-ray contrast agents. The methods of the present invention provide certain advantages over known such methods.

DESCRIPTION OF RELATED ART

The use of iopamidol as a contrast agent (e.g. in X-ray imaging) is well established. Iopamidol has the following structure and is referred to here as a compound of Formula (III):

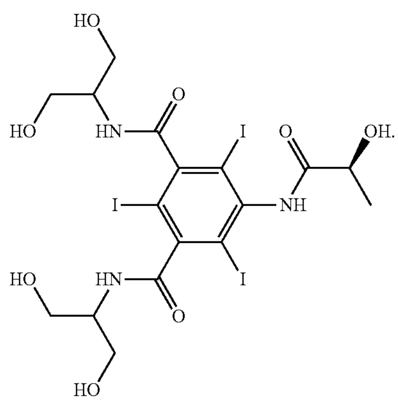

The manufacture of iopamidol involves the production of the compound of Formula (III) followed by the preparation of a formulation for use as a contrast agent. The chemical compound is usually made in a multistep synthesis and then purified before being used in the formulation. In each of the synthesis steps it is important to optimize the yield and minimize the production of impurities. For steps in which expensive reagents are used, it is particularly important to optimize usage of those reagents. The iodination reagents are expensive and thus the triiodination of the aromatic ring is an important step, generally performed at a late stage in the overall synthesis. In this step it is especially important to obtain a high yield with few impurities and minimal wastage of the iodination agent.

Iopamidol has previously been manufactured by processes such as that depicted in the reaction scheme in FIG. 1. Such a process is described, for example, in WO 02/44132 A1. This process has the disadvantage that it requires the use of solvents such as N,N-dimethylacetamide (DMAc) and hazardous and corrosive chemicals such as $SOCl_2$. Iopamidol has also previously been manufactured by the process depicted in the reaction scheme in FIG. 2. In this reaction scheme, an alkyl ester of 5-nitroisophthalic acid is first reacted with 2-amino-1,3-propanediol (serinol) to give the compound 5-amino-N, N'-bis(1,3-dihydroxypropan-2-yl) isophthalamide (also known as 1,3-ABA). 1,3-ABA is then iodinated using iodine monochloride. The free hydroxyl groups in the resulting compound are protected in several different ways, e.g. with acetone to give an acetal, with acid anhydride to give an ester or with an alkyl or aryl phosphoric acid to give a phosphate ester. The protected intermediate is then N-acylated with 2-acetyloxypropanoyl chloride (APC), deprotected and hydrolysed to give iopamidol.

There is a need for an improved process for the production of iopamidol. The process of the invention meets this need.

The present invention provides advantages over the above processes for producing iopamidol. For example, the process of the present invention may be carried out in solvents that are easily accessible, non-restricted and more environmentally friendly than those previously used. In addition, the process of the present invention may be carried out in fewer process steps than previous processes, which provides significant costs savings. In particular, compared to the reaction scheme shown in FIG. 2, the process of the present invention avoids the need for a protection step before reacting with APC.

SUMMARY OF THE INVENTION

In one aspect the present invention provides a process for the preparation of a compound of Formula (II):

Formula (II)

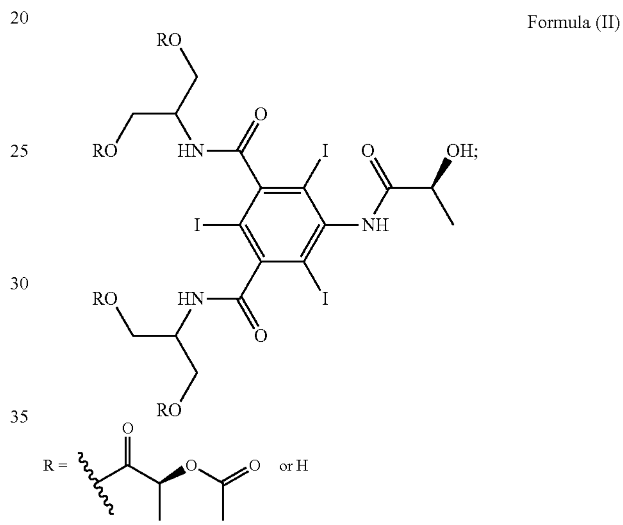

wherein the process comprises:

(i) reacting a compound of Formula (I) with pyridine and 2-acetyloxypropanoyl chloride (APC) to give a compound of Formula (II), wherein the compound of Formula (I) has the following structure:

Formula (I)

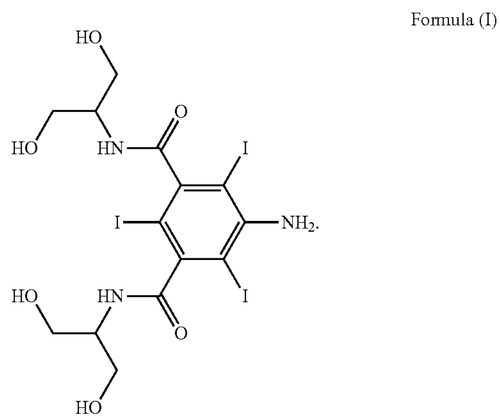 [SMILES: Nc1c(I)c(C(=O)NC(CO)CO)c(I)c(C(=O)NC(CO)CO)c1I]

In another aspect the present invention provides a compound or a formulation produced by the process of the invention.

The present invention also provides for use of a compound of Formula (II) as an intermediate in a process for the production of iopamidol of Formula (III):

Formula (II)

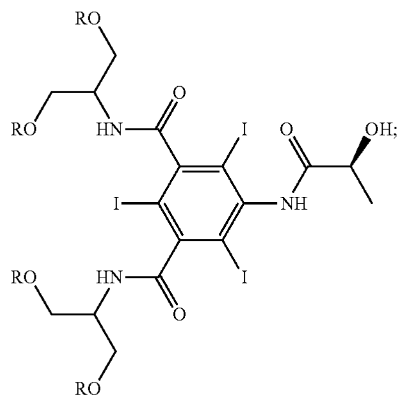

Formula (III)

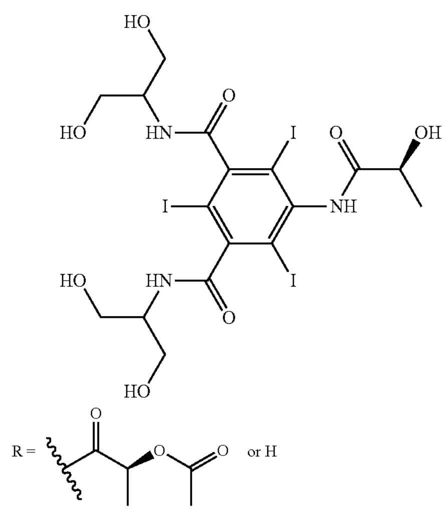

or H

The present invention has advantages compared to prior methods. The use of OH-protecting groups is avoided, which would introduce an additional protecting step, and potentially an additional deprotecting step in the reaction sequence. The use of high boiling solvents like DMAc or DMF, which are under strict restrictions by the REACH Directive, is also avoided, which in turn inhibits the formation of certain impurities. Furthermore, the process gives short reaction times without the use of expensive and toxic catalysts like DMAP, etc.

DETAILED DESCRIPTION OF THE PREFERRED EMBODIMENTS

The present invention relates to a process for the preparation of a compound of Formula (II):

Formula (II)

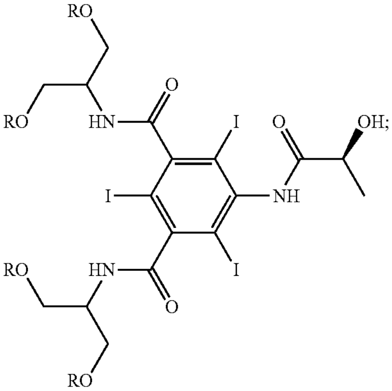

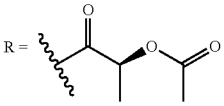

or H wherein the process comprises: (i) reacting a compound of Formula (I) with pyridine and 2-acetyloxypropanoyl chloride (APC) to give a compound of Formula (II), wherein the compound of Formula (I) has the following structure:

Formula (I)

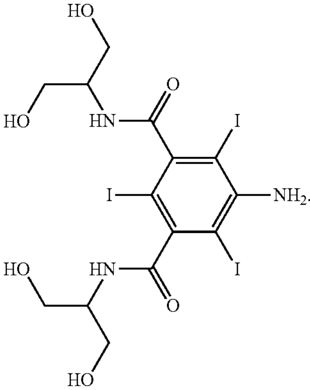

The process may further comprise the step of (ii) reacting the compound of Formula (II) with a hydrolysis agent to give a compound of Formula (III):

Formula (III)

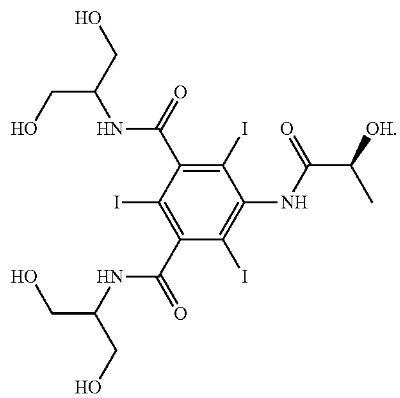 [SMILES: C[C@H](O)C(=O)Nc1c(I)c(C(=O)NC(CO)CO)c(I)c(C(=O)NC(CO)CO)c1I]

i.e. iopamidol

Figure 1:
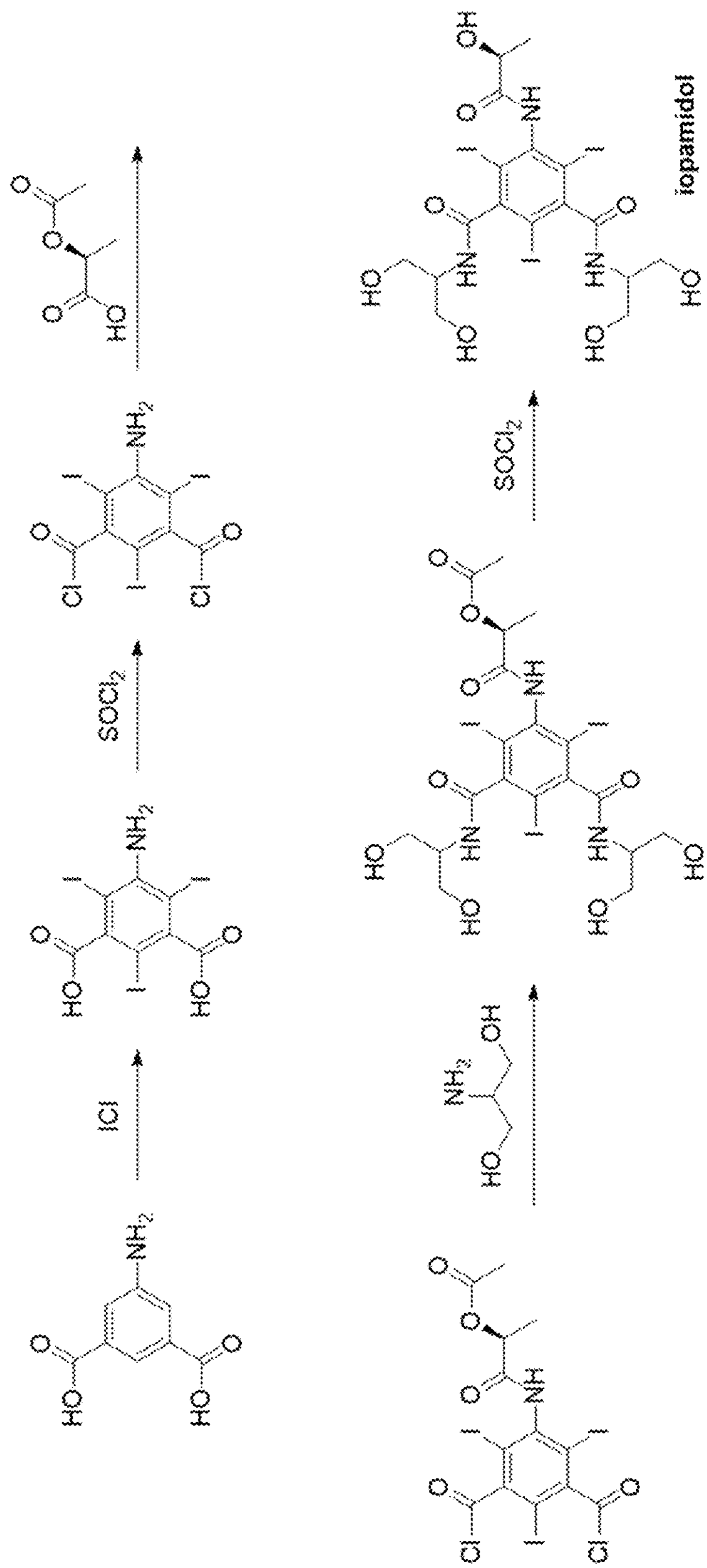
FIGS. 1 and 2 depict previous methods for the manufacture of Iopamidol.
Figure 2:
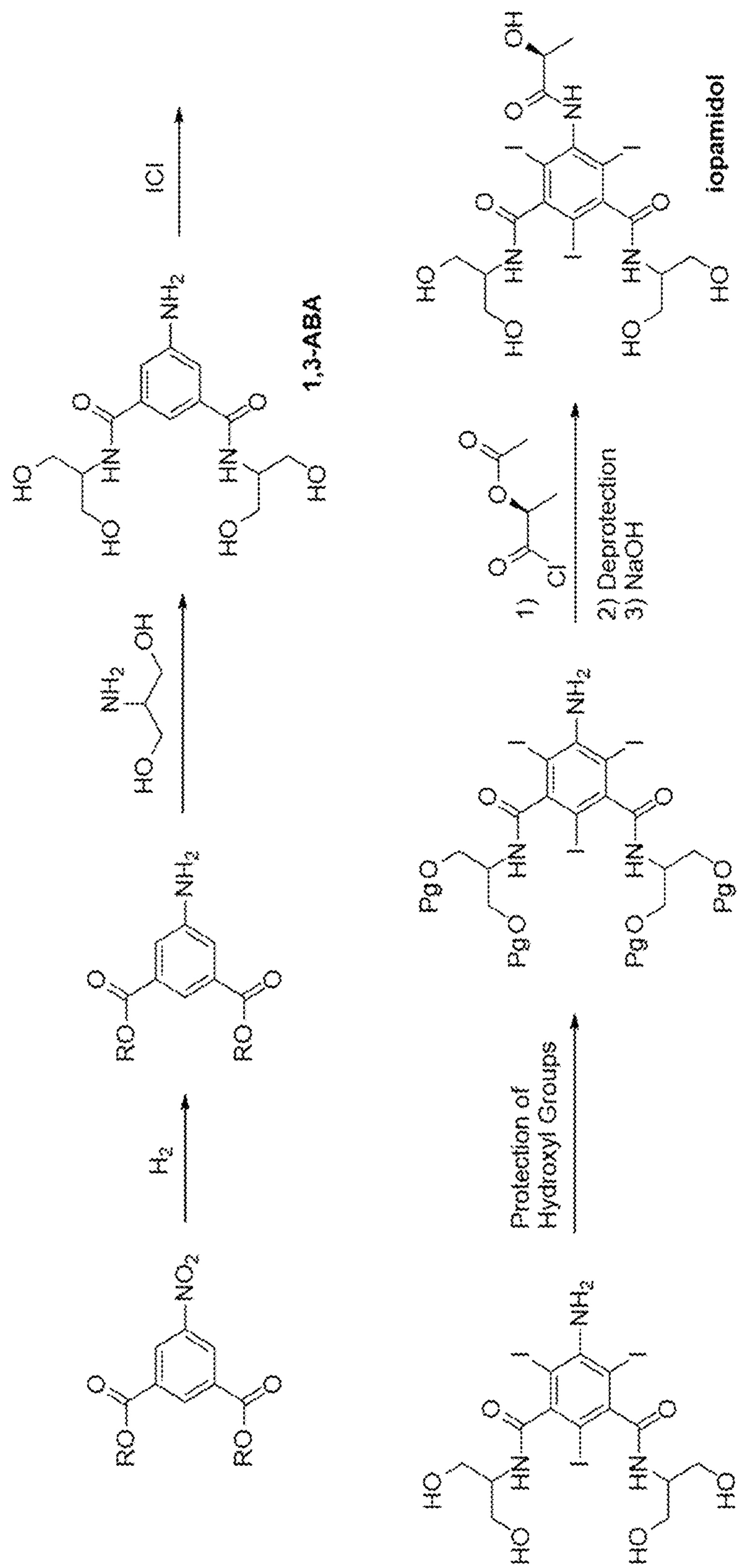
Figure 3:
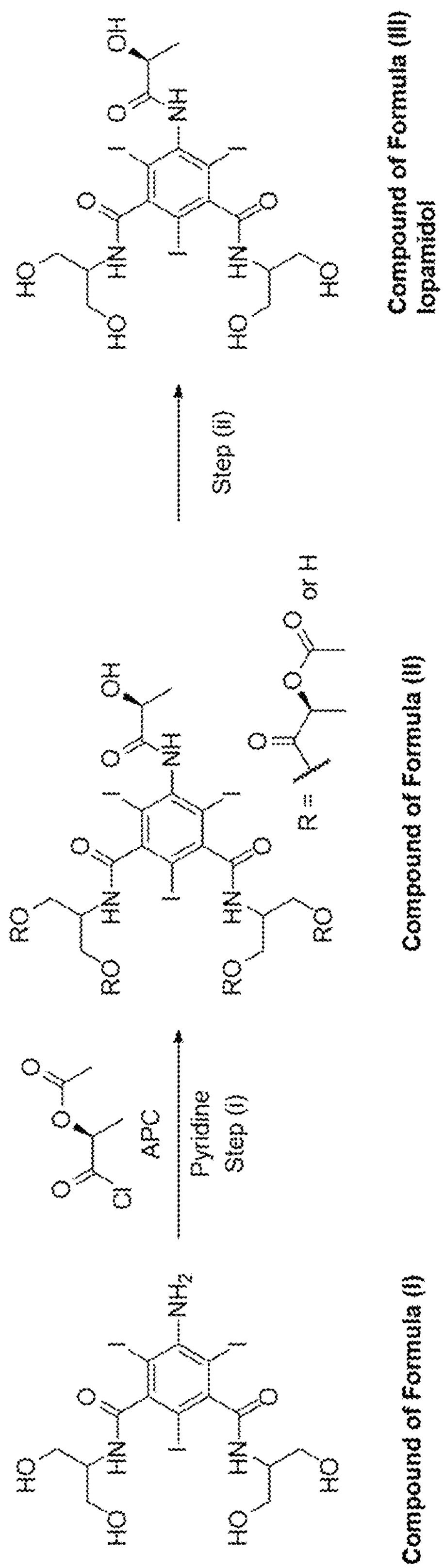
FIG. 3 shows a reaction scheme with steps that may be performed in the process of the present invention.

A reaction scheme showing steps that may be performed in the process of the present invention is set out in FIG. 3.

The starting compounds of the process of the invention may be made in any suitable way.

For example, N,N'-substituted 5-amino-1,3-benzenedicarboxamides (e.g. shown below as a compound of Formula (IV)) is known as an intermediate in the synthesis of iopamidol. These compounds may be used to prepare a compound of Formula (I) by iodination. In the formula below, R represents a 1,3-dihydroxy-2-propyl group (R=—$CH(CH_2OH)_2$) or a 2,3-dihydroxy-1-propyl group (R=—$CH_2CH(OH)CH_2(OH)$.

Formula (IV)

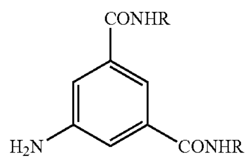

Compounds of Formula (IV) may be prepared starting from 5-nitro-1,3-benzenedicarboxylic acid dimethyl ester (shown below as a compound of Formula (V)), e.g. by amidation of the ester groups with 2-amino-1,3-dihydroxypropane (commonly known as serinol) or with 1-amino-2,3-dihydroxypropane (commonly known as isoserinol), followed by reduction of the 5-nitro group of the obtained N,N'-bis-substituted 5-nitro-1,3-benzenedicarboxamides. Alternatively, the reduction reaction step may be performed first, followed by the amidation reaction step.

Formula (IV)

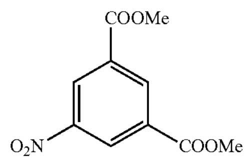

The amidation reaction in such processes is typically carried out with at least stoichiometric amounts of serinol or isoserinol (i.e. at least two moles of serinol or isoserinol per mol of 5-nitro-1,3-benzenedicarboxylic acid dimethyl ester), in the presence of a protic organic solvent, such as a lower alkanol, and at a temperature of from about 65° C. to about 150° C. Further details on such processes are provided in WO 02/44125 A1 and in WO 00/29372 A1.

N,N'-substituted 5-amino-1,3-benzenedicarboxamides (e.g. a compound of Formula (IV)) may also be prepared as described in WO 00/29372. For example, a di-lower-alkyl 5-nitroisophthalate may be reacted with at least two molar equivalents of a compound of the formula RNH2 (e.g., where R is $CH_2CH(OH)CH_2OH$ or $CH(CH_2OH)_2$) in a solvent comprising a lower-aliphatic alcohol containing a basic catalyst to obtain a solution containing 5-nitro-N,N'-bis(R)isophthalamide and, without isolating the latter, catalytically hydrogenating said solution to obtain a solution of 5-amino-N,N'-bis(R)-isophthalamide.

Further details on the process of the present invention are provided below. Any of the features provided below may be taken in combination with any other feature(s) provided below.

In the process, the compound of Formula (I) is reacted with pyridine and APC in step (i) in a solvent. The solvent in step (i) may be any suitable solvent, such as an aprotic solvent. The solvent in step (i) may be at least one of toluene, tetrahydrofuran (THF), acetonitrile, diethyl ether, methylethylketone, diglyme, glyme, dioxane, methylene chloride, chloroform, ethyl acetate, benzene, diisopropyl ether and acetone. The solvent in step (i) may be at least one of toluene, THF and acetonitrile. The solvent in step (i) may be acetonitrile.

Step (i) of the process may be carried out at any suitable temperature. For example, step (i) may be carried out at a temperature of: from 5° C. to 75° C., from 15° C. to 65° C., from 15° C. to 50° C., from 15° C. to 30° C., from 40° C. to 60° C. or from 20° C. to 30° C.

In step (i) of the process, the APC may be added to a mixture of the compound of at least the compound of Formula (I) and pyridine. In step (i) of the process, the APC may be added to the mixture of at least the compound of Formula (I) and pyridine over a period of 0 to 10 hours, 0.5 to 6 hours or 1 to 3 hours. The APC may be added in a first amount, followed by cooling and subsequent addition of APC in a second amount, where the first and second amounts may be the same or different. When the cooling takes place, it may be to a temperature of from 10 to 40° C. or to ambient temperature.

Pyridine has three important functions. Firstly, pyridine's main function is to work as a base as HCl is generated during the reaction. Free HCl will cause degradation of the compound of Formula (II). Secondly, pyridine is a co-solvent in the reaction. The compound of Formula (II) is difficult to dissolve with most organic solvents, including acetonitrile, but is soluble in pyridine. And thirdly, pyridine works as a catalyst in the reaction. As APC is added to the reaction mixture, it will first react with pyridine, forming an acyl pyridinium complex. The acyl pyridinium complex will then react with free hydroxyl-(OH) and amine ($NH_2$) groups in the compound of Formula (I), eventually giving the compound of Formula (II).

After the addition of the APC, the resulting reaction mixture may be maintained at a temperature of: from 5° C. to 75° C., from 5° C. to 70° C., from 5° C. to 95° C., from 15° C. to 75° C., from 15° C. to 65° C., from 15° C. to 60° C., from 15° C. to 50° C., from 15° C. to 30° C., from 40° C. to 60° C., from 20° C. to 40° C. or from 20° C. to 30° C. The resulting reaction mixture may be maintained at any of these temperatures for up to 24 hours or for 2 to 12 hours.

The compound of Formula (II) produced in step (i) of the process may be reacted in step (ii) of the process without being isolated. In particular, it is not necessary to purify the compound of Formula (II) produced in step (i) before further reaction.

Step (ii) of the process may be carried out at any suitable temperature. For example, step (ii) may be carried out at a temperature of: from 5° C. to 95° C., from 5° C. to 70° C., from 15° C. to 75° C., from 15° C. to 60° C., from 15° C. to 50° C., from 40° C. to 60° C. or from 20° C. to 40° C.

Step (ii) of the process may be carried out in acidic or basic conditions. When carried out under acidic conditions, any suitable acid may be used. For example, sulphuric acid and/or hydrochloric acid may be used as the hydrolysis agent.

In the process, the hydrolysis agent may be used with water in step (ii) to control the pH between 12 and 14. The hydrolysis agent may be used with water in step (ii) to control the pH between 12.8 and 13.7 or between 13 and 13.6 or at approximately 13.5.

The hydrolysis agent in step (ii) may be an aqueous base or a basic ion exchange resin. The hydrolysis agent in step (ii) may be aqueous NaOH, aqueous KOH or ammonia and/or combinations thereof. In particular, the hydrolysis agent in step (ii) may be aqueous NaOH.

The compound of Formula (III) may be purified. It is desirable that the compound of Formula (III) be purified to give a purity of at least 90%, at least 95% or at least 99.8%. The purification may be achieved using any suitable method of purification. One or more of the following purification methods may be used in any combination: desalination (e.g., electrodialysis or ion exchange resins), distillation, one or more columns (e.g. using Amberlite XAD1600N), evaporation of water, crystallization. For example, the compound of Formula (III) may be purified in accordance with the methods described in US 2011/017673 A1.

The compound of Formula (III) may be used to prepare a formulation, e.g. for use as a contrast agent. The formulation may be prepared by dissolving the formulation in a solvent (e.g. water). This allows the formulation to be injected into a subject.

In addition to the solvent, the formulation may further include one or more of a buffer, a complexing agent and a pH adjuster. The buffer may be tromethamine. The complexing agent may be calcium disodium EDTA. The pH adjuster may be hydrochloric acid and/or sodium hydroxide. The formulation may include a compound of Formula (III), water, tromethamine, calcium disodium EDTA and hydrochloric acid and/or sodium hydroxide.

The present invention also relates to a compound and/or formulation produced by the process described according to the invention. The present invention also relates to the use of a compound and/or formulation produced by the process of the invention. In particular, the compound and/or formulation may be used as a contrast agent (e.g. in a subject).

The present invention also relates to the use of a compound of Formula (II) as an intermediate in a process for the production of iopamidol.

EXAMPLES

The present invention is described with reference to the following examples.

Example 1

5-amino-N, N'-bis(1,3-dihydroxypropan-2-yl)-2,4,6-triiodoisophthalamide (30.0 g; 42.6 mmol), acetonitrile (93.0 g) and pyridine (18.5 g; 234 mmol) were added to a reactor with magnetic stirring. The reaction medium was heated to 67° C. and(S)-2-acetyloxypropanoyl chloride (22.0 ml; 174 mmol) was added over a period of 60 minutes. The reaction mixture was cooled down to 35° C. and an additional amount of(S)-2-acetyloxypropanoyl chloride (9.2 ml; 72.7 mmol) was added over a period of 60 minutes and was then left while stirring for another 18 hours. Water (150 ml) was added followed by careful addition of 50% NaOH (54.4 g; 680 mmol). The pH was then adjusted to 13.5 using additional amounts of 50% NaOH and stirred for 45 min. The reaction mixture was neutralized to pH 7.0 using 35% HCl and the organic solvent was distilled off under reduced pressure to give iopamidol with 91.6% HPLC purity. The iopamidol product can be further purified using conventional purification methods.

Example 2

5-amino-N,N'-bis(1,3-dihydroxypropan-2-yl)-2,4,6-triiodoisophthalamide (30.1 g; 42.7 mmol), acetonitrile (93.0 g) and pyridine (20.4 g; 258 mmol) were added to a reactor with magnetic stirring. The temperature of the reactor was set to 67.5° C. and(S)-2-acetyloxypropanoyl chloride (31.2 ml; 246 mmol) was added over a period of 60 minutes. 4 hours after the addition, the reactor was cooled down to ambient temperature and water (150 ml) was added followed by careful addition of 50% NaOH (54.4 g; 680 mmol). The pH was then adjusted to 13.5 using additional amounts of 50% NaOH and stirred for 30 min. The reaction mixture was neutralized to pH 6.5 using 35% HCl and the organic solvent was distilled off under reduced pressure to give iopamidol with 91.2% purity. The iopamidol product can be further purified using conventional purification methods.

Example 3

5-amino-N, N'-bis(1,3-dihydroxypropan-2-yl)-2,4,6-triiodoisophthalamide (30.0 g; 42.6 mmol), acetonitrile (93.0 g) and pyridine (18.5 g; 234 mmol) were added to a reactor with magnetic stirring. The temperature of the reactor was set to 60° C. and(S)-2-acetyloxypropanoyl chloride (30.6 ml; 242 mmol) was added over a period of 60 minutes. 5 hours after the addition, the reactor was cooled down to ambient temperature and water (150 ml) was added followed by careful addition of 50% NaOH (53.2 g; 665 mmol). The pH was then adjusted to 13.5 using additional amounts of 50% NaOH and stirred for 30 min. The reaction mixture was neutralized to pH 7.0 using 35% HCl and the organic solvent was distilled off under reduced pressure to give iopamidol with 92.5% purity. The iopamidol product can be further purified using conventional purification methods.

Example 4

5-amino-N,N'-bis(1,3-dihydroxypropan-2-yl)-2,4,6-triiodoisophthalamide (40.0 g; 56.7 mmol), acetonitrile (124 g) and pyridine (20.7 g; 262 mmol) were added to a reactor with magnetic stirring. The temperature of the reactor was set to 25° C. and(S)-2-acetyloxypropanoyl chloride (43.5 ml; 344 mmol) was added over a period of 30 min. The reaction mixture was stirred at 25° C. over a period of 23 hours and water (100 ml) was added. 50% NaOH (76.0 g; 950 mmol) was slowly added to the reaction mixture giving a pH of 11.7. The pH was then adjusted to 13.6 by careful addition of more 50% NaOH. After stirring for 30 minutes, the pH was adjusted to 6.9 using 35% HCl and the organic solvent was distilled off under reduced pressure. The crude product was desalinated using electrodialysis and ion exchange resins (Purolite PPC150 and Purolite A847), and further purified by passing the solution through a column with Amberlite XAD1600N, followed by evaporation of water to give iopamidol with 98.2% purity.

Example 5

5-amino-N, N'-bis(1,3-dihydroxypropan-2-yl)-2,4,6-triiodoisophthalamide (3.53 g; 5.00 mmol), toluene (8.67 g) and pyridine (2.38 g; 30.0 mmol) were added to a round-bottom flask with magnetic stirring. (S)-2-acetyloxypropanoyl chloride (4.04 ml; 31.9 mmol) was added over a period of 60 min and the reaction mixture was left stirring at ambient temperature over a period of 18 hours. Water (40 ml) and methanol (40 ml) were added and the pH was adjusted to and maintained at 13.5 by the addition of 25% NaOH. After stirring for 30 minutes, the reaction mixture was neutralized to pH 7 with acetic acid and concentrated under reduced pressure to give iopamidol with 57% HPLC purity as a dark brown residue. The iopamidol product can be further purified using conventional purification methods.

Example 6

5-amino-N, N'-bis(1,3-dihydroxypropan-2-yl)-2,4,6-triiodoisophthalamide (3.53 g; 5.00 mmol), THF (8.88 g) and pyridine (2.38 g; 30.0 mmol) were added to a round-bottom flask with magnetic stirring. (S)-2-acetyloxypropanoyl chloride (4.04 ml; 31.9 mmol) was added over a period of 60 min and the reaction mixture was left stirring at ambient temperature over a period of 18 hours. Water (50 ml) and methanol (20 ml) were added and the pH was adjusted to and maintained at 13.5 by the addition of 25% NaOH. After stirring for 30 minutes, the reaction mixture was neutralized to pH 7 with acetic acid and concentrated under reduced pressure to give iopamidol with 74% HPLC purity as a yellow residue. The iopamidol product can be further purified using conventional purification methods.

It will be understood by a person skilled in the art that the Examples, as usual, have been performed on a laboratory scale and that the conditions used may be adapted when putting the invention into practice on an industrial scale.

The invention claimed is:

1. A process of preparing a compound of

Formula (III)

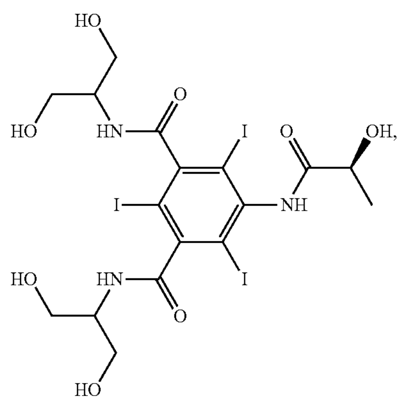

wherein the process comprises:

(i) contacting 2-acetyloxypropanoyl chloride (APC) with a mixture comprising a compound of Formula (I) in a solvent system comprising pyridine, to generate a compound of Formula (II), wherein the compound of Formula (I) has the following structure:

Formula (I)

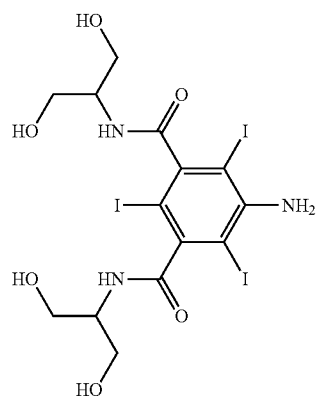

(ii) reacting the compound of Formula (II) with a hydrolysis agent to give a compound of Formula (III), wherein the compound of Formula (II) has the following structure:

Formula (II)

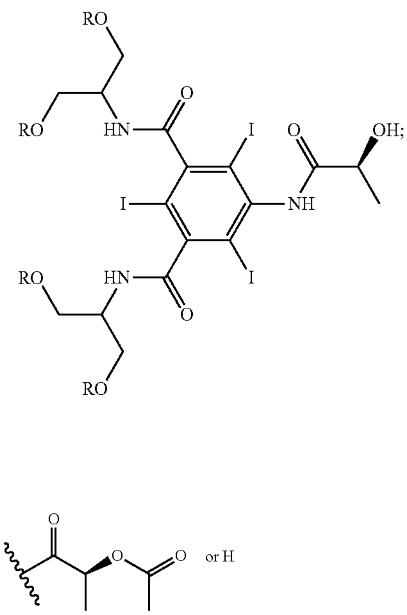

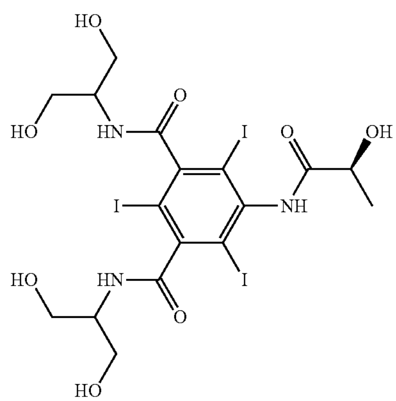 [SMILES: C[C@H](O)C(=O)Nc1c(I)c(C(=O)NC(CO)CO)c(I)c(C(=O)NC(CO)CO)c1I]

wherein the hydrolysis is maintained at a pH within about 12.0 to about 14.0 and wherein the amidation and hydrolysis are carried out in one vessel without isolation of the amidation product.

2. The process of claim 1, wherein the hydrolysis agent is used with water in step (ii) to control the pH.

3. The process of claim 1, wherein the hydrolysis agent in step (ii) is:

(a) an aqueous base or a basic ion exchange resin; or (b) aqueous NaOH, aqueous KOH or ammonia and/or combinations thereof; or (c) aqueous NaOH.

4. The process of claim 1, wherein step (ii) is carried out at a temperature of from 5° C. to 95° C.

5. The process of claim 1, wherein the compound of Formula (III) is purified.

6. The process of claim 1, wherein the compound of Formula (III) is dissolved in a solvent to produce a formulation, wherein:

(i) the formulation further comprises a solvent; and/or (ii) the formulation further comprises a buffer; and/or (iii) the formulation further comprises a complexing agent; and/or (iv) the formulation further comprises a pH adjuster.

7. A method of preparing iopamidol of Formula (III):

Formula (III)

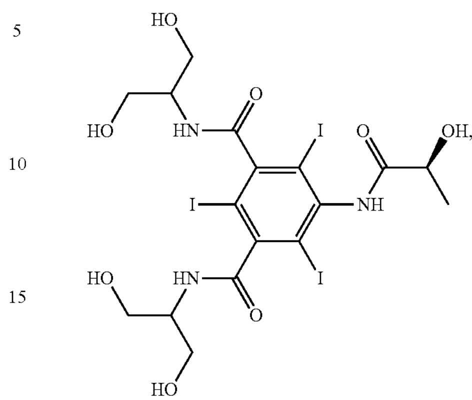

comprising using an intermediate of Formula (II):

Formula (II)

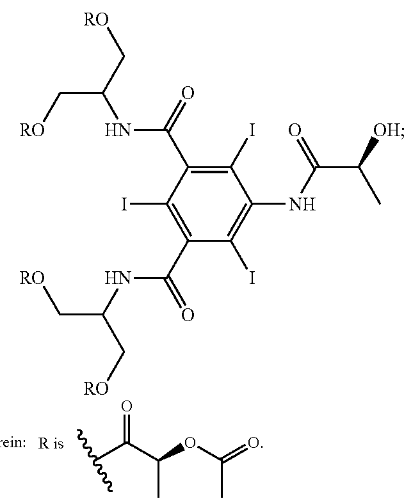

wherein: R is

8. The process of claim 1, wherein the hydrolysis is conducted at a temperature of about 35° C.-about 55° C.

9. The process of claim 5, wherein the purification includes one or more of: desalination, resin treatment, distillation or crystallization.

* * * * *